United States Patent
Beck et al.

(10) Patent No.: US 10,869,724 B2
(45) Date of Patent: Dec. 22, 2020

(54) SAGITTAL ROTATION DETERMINATION

(71) Applicants: Smith & Nephew, Inc., Memphis, TN (US); Smith & Nephew Asia Pacific Pte. Limited, Singapore (SG); Smith & Nephew Orthopaedics AG, Zug (CH)

(72) Inventors: Steffen Beck, Munich (DE); Mario Schubert, Poing (DE); Christian Brack, Neusäß (DE); Luise Poitzsch, Osnabrück (DE)

(73) Assignees: Smith & Nephew, Inc., Memphis, TN (US); Smith & Nephew Asia Pacific Pte. Limited, Singapore (SG); Smith & Nephew Orthopaedics AG, Zug (CH)

( * ) Notice: Subject to any disclaimer, the term of this patent is extended or adjusted under 35 U.S.C. 154(b) by 88 days.

(21) Appl. No.: 16/306,991

(22) PCT Filed: Mar. 1, 2018

(86) PCT No.: PCT/EP2018/055067
§ 371 (c)(1),
(2) Date: Dec. 4, 2018

(87) PCT Pub. No.: WO2018/162322
PCT Pub. Date: Sep. 13, 2018

(65) Prior Publication Data
US 2020/0305976 A1    Oct. 1, 2020

(30) Foreign Application Priority Data

Mar. 9, 2017   (WO) .................. PCT/EP2017/055583

(51) Int. Cl.
*A61B 6/00*      (2006.01)
*A61B 34/10*     (2016.01)
(Continued)

(52) U.S. Cl.
CPC .............. *A61B 34/10* (2016.02); *A61B 6/582* (2013.01); *G06T 3/60* (2013.01); *G06T 7/0014* (2013.01);
(Continued)

(58) Field of Classification Search
CPC ......... A61B 6/505; A61B 6/583; A61B 6/582; A61B 8/0875; G06T 7/0012;
(Continued)

(56) References Cited

U.S. PATENT DOCUMENTS 7,688,998 B2   3/2010 Tama et al.
7,922,391 B2   4/2011 Essenreiter et al.
(Continued)

FOREIGN PATENT DOCUMENTS

EP      1563799 A1   2/2004
EP      2119397 A1   11/2009
(Continued)

OTHER PUBLICATIONS

Yamato et al., Calculation of the Target Lumbar Lordosis Angle for Restoring an Optimal Pelvic Tilt in Elderly Patients With Adult Spinal Deformity, Feb. 15, 2016 [retrieved Aug. 9, 2020], Spine, vol. 41, Issue 4, pp. E211-E217. doi: 10.1097/BRS.0000000000001209 (Year: 2016).*

(Continued)

*Primary Examiner* — Andrew M Moyer
*Assistant Examiner* — Dennis Rosario
(74) *Attorney, Agent, or Firm* — Troutman Pepper Hamilton Sanders LLP

(57) ABSTRACT

The invention relates to a method of determining the sagittal rotation of a patient's pelvis based on a standard anterior posterior X-ray-image with known image parameters and a calibration of the image, for example by using at least one King-Mark calibration object. The angle of the pelvic rota- (Continued)

tion is determined between a pelvic plane which is orthogonal to the midsagittal plane of the pelvis, and the image plane of the X-ray-image. Assuming the patient's position shown on the X-ray-image represents a standard neutral position, the X-ray-image plane can be used as a functional reference plane for further calculations, for example during hip-replacement surgery. The present invention further relates to a corresponding computer program and system.

20 Claims, 6 Drawing Sheets

(51) Int. Cl.
G06T 3/60 (2006.01)
G06T 7/00 (2017.01)
G06T 11/00 (2006.01)

(52) U.S. Cl.
CPC ....... *G06T 11/005* (2013.01); *A61B 2034/102* (2016.02); *A61B 2034/105* (2016.02); *A61B 2034/107* (2016.02); *G06T 2207/10116* (2013.01); *G06T 2207/20101* (2013.01); *G06T 2207/30008* (2013.01)

(58) Field of Classification Search
CPC . G06T 2207/30008; G06T 2207/10116; G06T 2207/10081; G06T 2207/30004; G06T 7/20
See application file for complete search history.

(56) References Cited

U.S. PATENT DOCUMENTS

| 8,075,184 | B2 | 12/2011 | King et al. |
| 2013/0304429 | A1 | 11/2013 | Haimerl |
| 2015/0313566 | A1 | 11/2015 | Helmut et al. |
| 2018/0000447 | A1 | 1/2018 | Stindel et al. |

FOREIGN PATENT DOCUMENTS

| WO | 2011092531 A1 | 8/2011 |
| WO | 2014127354 A1 | 8/2014 |
| WO | 2016116232 A1 | 7/2016 |
| WO | 2016186969 A1 | 11/2016 |

OTHER PUBLICATIONS

Szuper et al., Three-dimensional quantitative analysis of the proximal femur and the pelvis in children and adolescents using an upright biplanar slot-scanning X-ray system, Aug. 26, 2014 [retri Aug. 9, 2020], Pediatric Radiology, vol. 45, pp. 411-421. https://doi.org/10.1007/s00247-014-3146-2 (Year: 2014).*
Monazzam et al., Reliability of Overcoverage Parameters With Varying Morphologic Pincer Features: Comparison of EOS and Radiography, May 9, 2013 [retrieved Aug. 9, 2020], Clinical Orthopaedics and Related Research, vol. 471, pp. 2578-2585. https://doi.org/10.1007/s11999-013-3001-z (Year: 2013).*
Tannast et al., Estimation of pelvic tilt on anteroposterior X-rays—a comparison of six parameters, Dec. 20, 2005 [retrieved Aug. 10, 2020], Skeletal Radiology, vol. 35, pp. 149-155. Retrieved: https://link.springer.com/article/10.1007/s00256-005-0050-8 (Year: 2005).*
Lucas et al., Estimation of Transverse Plane Pelvic Rotation Using a Posterior-Anterior Radiograph, Jan. 1, 2005 [retrieved Aug. 9, 2020], Spine, vol. 30, Issue 1,pp. E20-E27. Retrieved: https://journals.lww.com/spinejournal/Fulltext/2005/01010/Estimation_of_Transverse_Plane_Pelvic_Rotation.30.aspx (Year: 2005).*
European Patent Office, International Search Report and Written Opinion for corresponding to PCT/EP2018/055067, dated May 24, 2018, 1-9 pages.
Yaniv, "Fluoroscopic X-ray Image Processing and Registration for Computer-Aided Orthopedic Surgery" Institute of Computer Science, The Hebrew Univeristy of Jerusalem, Jerusalem, Israel, Oct. 1, 1998, pp. 1-65.
Tannast et al. Estimation of pelvic tilt on anteroposterior X-rays—a comparison of six parameters, Department of Diagnostic, Interventional and Pediatric Radiology, University of Bern, Bern, Switzerland, Skeletal Radiol DOI 10.1007/x00256-005-0050-8 Scientific Article, pp. 1-7.
Ehlke et al., "Towards Robust Measurement of Pelvic Parameters from AP Radiographs using Articulated 3D Models", Konrad-Zuse-Zentrum für Informationstechnik, Feb. 2015, ZIB-Report ISSN1438-0064, 1-6 pages, Berlin-Dahlem, Germany.
Tasi "An Efficient and Accurate Camera Calibration Techique for 3D Machine Vision", IBM, T.J. Watson Research Center, Yorktown Heights, NY. CH2290-5/86/0364, 1986, IEEE, pp. 364-374., New York, USA.
Tasi, "A Versatile Camera Calibration Technique for High-Accuracy 3D Machine Vision Metrology Using Off-the-Shelf TV Cameras and Lenses", IEEE Journal of Robotics and Automation, vol., RA-3, No. 4, Aug. 1987, pp. 323-344 USA.

* cited by examiner

SAGITTAL ROTATION DETERMINATION

RELATED APPLICATION DATA

This application is a national phase application of International Application No. PCT/EP2018/055067 filed Mar. 1, 2018, claiming priority from PCT/EP2017/055583 filed Mar. 9, 2017 and published in the English language.

TECHNICAL FIELD

The present invention relates to a computer implemented method for determining the sagittal rotation of a patient's pelvis and to a corresponding computer program and system.

SUMMARY

In medical procedures concerning the pelvis of a patient, for example hip-replacement surgery, it is desirable to know how the pelvis is orientated with respect to other anatomical structures such as the femurs for a specific patient and for different postures, particularly for a standing posture of the patient. In the particular case of hip-replacement surgery it is an ultimate goal to orient the artificial hip-joint components with respect to the pelvis such that the patient can move in a usual manner after surgery without the hip joints range of motion being negatively constrained with respect to the pre-operative range of motion.

A prior art approach for determining an implant orientation is to determine the pelvic tilt angle, i.e. the angle between the anterior pelvic plane (APP) and the patient's coronal plane in a standing posture of the patient, whereupon the anterior pelvic plane is used as a reference plane for aligning the artificial joint components. For determining the pelvic tilt, an X-ray-image taken in an anterior-posterior direction can however provide only a very rough estimation of the tilt angle. For determining the pelvic tilt more precisely, it is therefore necessary to acquire additional pre-operative X-ray-images of the standing patient's pelvis in a lateral direction, or even performing a pre-operative CT-scan. These approaches however induce an increased and therefore unwanted radiation exposure of the patient.

The present invention allows for precisely determining the sagittal rotation of a patient's pelvis without imposing additional radiation exposure on the patient.

The method, the program and the system are defined by the appended independent claims. Advantages, advantageous features, advantageous embodiments and advantageous aspects of the present invention are disclosed in the following and contained in the subject-matter of the dependent claims. Different advantageous features can be combined in accordance with the invention wherever technically expedient and feasible. Specifically, a feature of one embodiment which has the same or a similar function to another feature of another embodiment can be exchanged with said other feature, and a feature of one embodiment which adds an additional function to another embodiment can in particular be added to said other embodiment.

According to a first aspect of the present invention a computer implemented method for determining the sagittal rotation of a patient's pelvis is provided, wherein the method comprises the steps of:

acquiring image data describing a two-dimensional X-ray-image of the patient's pelvis made in an anterior-posterior direction;

determining, based on the image data, position data describing the position of a plurality of pelvic landmarks reproduced in or derivable from the two-dimensional X-ray-image;

acquiring calibration data describing the position of a calibration plane with respect to the patient's pelvis, the calibration plane being perpendicular to the anterior-posterior direction;

determining, based on the position data and the calibration data, calibrated projection data describing a two-dimensional projection representing the plurality of pelvic landmarks of the actual patient's pelvis being projected into the calibration plane in the anterior-posterior direction;

acquiring distance data describing at least one of a medial-lateral distance and a cranial-caudal distance between at least one first pelvic landmark and at least one second pelvic landmark in the calibrated two-dimensional projection;

acquiring, from a database, regression data describing a correspondence, particularly a linear correspondence between at least one of said medial-lateral distances and cranial-caudal distances, and a pelvic sagittal rotation;

determining, based on the distance data and the regression data, the sagittal rotation of the patient's pelvis.

In other words, an X-ray-image of the patient's pelvis is acquired in an anterior-posterior direction, and at least two landmarks are identified in the X-ray-image. For example, such landmarks are prominent features of the patient's pelvis. Additionally or alternatively, landmarks can also be calculated from such prominent features; for example, the center of rotation of the hip joint can be calculated from the location of points on the surface of the acetabulum, which can be identified in the X-ray-image.

Further, a calibration plane is defined with respect to the pelvis, such that the landmarks can be projected into that calibration plane. In a preferred embodiment, the calibration plane's position is defined such that it includes the centers of rotation of at least one acetabulum. Assuming that the radiation source for acquiring the X-ray-images is represented by a punctiform source, it becomes apparent that the image of the pelvis acquired via such source is somehow "distorted", depending on the distance between the radiation source and the depicted features of the pelvis. To compensate for such image distortion, landmarks which are of interest for later procedures are virtually projected into the calibration plane as if the landmarks of the (actual) pelvis are projected into the calibration plane solely in an anterior-posterior direction. In other words, a "parallel projection" of the "landmark-array" of the three-dimensional pelvis into the calibration plane in an anterior-posterior direction is determined.

With the quasi parallel projection being determined, the projected image serves for distance measurements within the calibration plane and between the at least two landmarks.

Further, a database is provided which comprises a plurality of reference patient datasets which not only include the same distance measurements for a plurality of reference patients, but also a determined value for the sagittal rotation of the pelvis of each reference patient. The database therefore provides a correlation between inter-landmark-distances within the calibration plane and the sagittal rotation of the pelvis for each reference patient.

A comparison between the distances measured for the current patient and corresponding distances determined for the reference patients ultimately allows for deriving the sagittal rotation angle for the current patient from the statistical data provided by the reference database.

According to a first alternative embodiment of the present invention, "meaningful" distance measurements between pelvic landmarks within the calibration plane are only possible when the exact distance between the calibration plane and the X-ray-source is determined. For determining the position of the calibration plane with respect to the radiation source, at least one calibration feature of a predetermined size and/or geometry may be used, which is reproduced in the X-ray-image. The known distance between the radiation source and the image plane and the known size and/or geometry of such calibration features allows to calculate, from the features' depiction in the X-ray-image, the position of these features with respect to the radiation source in three-dimensional space and therefore defines the position of the calibration plane in three-dimensional space. It is however also possible to provide such features in an anterior and in a posterior location with respect to the pelvis. Such calibration features are for example described in U.S. Pat. No. 8,075,184. The calibration features disposed anterior to the pelvis may define a first, anterior reference plane, whereas the calibration features disposed posterior to the pelvis may define a second, posterior reference plane. Both positions of the reference planes are known in three-dimensional space. Knowing the ratio of the A-P-distance from the calibration plane to the anterior plane and the A-P-distance between both reference planes, the relative position of the calibration plane between both reference planes can be defined and as result the calibration plane is defined in three-dimensional space. The ratio of the reference planes and the calibration plane are taken from a database.

It is however also necessary to know the distance of each of the anatomical landmarks in an anterior-posterior direction with respect to the calibration plane. The distance of each landmark with respect to the calibration plane may be taken from a database containing predefined values for the anterior-posterior-distances of a plurality of pelvic landmarks. In the alternative, the A-P-distance can be acquired by matching a three-dimensional pelvis model which may in turn be acquired from an anatomical atlas, to the two-dimensional X-ray-image. This pelvis model specifies the position of the plurality of pelvic landmarks and therefore may also specify the A-P-distances of each of the pelvic landmarks with respect to a predefined plane. Therefore, the necessary A-P-distances of the landmarks of the current patient can be identified from statistical values provided by that database.

For the above described embodiment, the setup geometry between the X-ray-source, the pelvis landmarks and the image plane is known. From this known setup geometry, "parallel projection" of the pelvis into any arbitrary calibration plane that is parallel to the image plane can be calculated. This "parallel projection" is now free from any shift or distortion caused by the "conical" X-ray-projection and finally allows for meaningful distance measurements between pelvic landmarks within the calibration plane.

While the above-described first embodiment requires the distance between the X-ray-source and the detector plane to be determined, the following alternative second embodiment does not. As already described further above, the calibration features disposed anterior to the pelvis may define a first, anterior reference plane, whereas the calibration features disposed posterior to the pelvis may define a second, posterior reference plane. For both reference planes the magnification factor/distortion factor is known because of the known size of the calibration feature. Likewise each landmark defines a landmark plane which is positioned between the two reference planes.

Knowing the ratio of the A-P-distance from one of the calibration features to one of the landmarks and the A-P-distance between both calibration features the relative position of each landmark plane between the reference planes can be defined. The ratios of the landmarks and calibration spheres are taken from a database.

Due to the projective nature of the X-ray the magnification factor increases linear between the punctiform source and the detector plane and therefore it also increases linear between the anterior and the posterior reference plane. Because the relative position of the each landmark plane between the anterior and posterior reference planes is known and the relative position correlates linear with the magnification factor, the magnification factor of each landmark plane can be defined.

Generally spoken trough each landmark a plane can be drawn which is parallel to one of the reference planes and for each of those planes it is known how an object in this plane is magnified. Therefore the true size of an object being positioned in one of those planes is known which allows for meaningful distance measurements between pelvic landmarks.

The landmarks can either be identified manually, for example by a practitioner palpating depictions of the landmarks within the original X-ray-image or the already "calibrated" image. In the alternative, the landmarks can be identified automatically by matching a three-dimensional pelvis model acquired from an anatomical atlas to the two-dimensional image.

The position of the landmarks within the image can then be derived from the anatomical atlas which indicates the position of the landmarks within the model of the pelvis.

According to a preferred embodiment of the present invention, the pelvic landmarks are selected from the group consisting of:
  left anterior superior iliac spine, right anterior superior iliac spine;
  left iliosacral joint, right left iliosacral;
  left lateral foramen point, right lateral foramen point;
  cranial edge of pubic symphysis; and
  center of rotation of left acetabulum, center of rotation of right acetabulum.

Of course, any other pelvic landmark that is suitable for distance measurements may be acquired, as well.

According to a further preferred embodiment of the present invention, distances between the anatomical landmarks are measured in a cranial-caudal/vertical direction and/or in a medial-lateral/horizontal direction. The distance measurements may be selected from the group consisting of:
  medial-lateral distance between left anterior superior iliac spine and right anterior superior iliac spine;
  cranial-caudal distance between iliosacral joint and line connecting anterior superior iliac spines;
  cranial-caudal distance between center of rotation of left or right acetabulum and line connecting anterior superior iliac spines;
  cranial-caudal distance between center of rotation of left or right acetabulum and line connecting left lateral foramen point and right lateral foramen point;
  medial-lateral distance between center of rotation of left or right acetabulum and midsagittal plane of patient; and cranial-caudal distance between center of rotation of left or right acetabulum and cranial edge of pubic symphysis.

Again, any other suitable distance measurement between identified landmarks may be performed in the context of the present invention.

As already set out further above, it is desirable to know the sagittal rotation of the patient's pelvis when the patient takes a standing posture. Even though the present invention can be performed for any posture of the patient, it is the standing posture which is most desirable.

With the necessary distance measurements acquired for the current patient, the determined values for each measurement can be compared to a statistical distribution obtained from corresponding measurements performed on a plurality of reference patients. From the measurements taken in a medial-lateral direction, it is possible to derive a common basis for comparing a plurality of pelvic bones, irrespective of the actual size of the bone and the measured cranial-caudal distances resulting therefrom. The measurements taken in a cranial-caudal direction then give a direct indication how much the pelvis is rotated in the midsagittal plane. As, according to the present invention, the database further provides a correlation between the measured distances in the cranial-caudal direction, and the sagittal rotation of the pelvis, the sagittal rotation of the current patient's pelvis can be finally derived from the database.

In particular, the pelvic sagittal rotation may define the angle between the coronal plane of the patient and an AAC-plane containing the left anterior superior iliac spine, the right anterior superior iliac spine, and at least one of the center of rotation of the left acetabulum and the center of rotation of the right acetabulum.

Further, the determined AAC-plane may serve as a reference basis for a registration procedure for surgery, particularly for hip replacement surgery.

Definitions

The method in accordance with the invention is for example a computer implemented method. For example, all the steps or merely some of the steps (i.e. less than the total number of steps) of the method in accordance with the invention can be executed by a computer (for example, at least one computer). An embodiment of the computer implemented method is a use of the computer for performing a data processing method. An embodiment of the computer implemented method is a method concerning the operation of the computer such that the computer is operated to perform one, more or all steps of the method.

The computer for example comprises at least one processor and for example at least one memory in order to (technically) process the data, for example electronically and/or optically. The processor being for example made of a substance or composition which is a semiconductor, for example at least partly n- and/or p-doped semiconductor, for example at least one of II-, III-, IV-, V-, VI-semiconductor material, for example (doped) silicon and/or gallium arsenide. The calculating steps described are for example performed by a computer. Determining steps or calculating steps are for example steps of determining data within the framework of the technical method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term "cloud computer" includes a cloud computer system which for example comprises a system of at least one cloud computer and for example a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (world wide web). For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical) analytical devices (such as for example devices for performing (medical) imaging methods), wherein the technical signals are for example electrical or optical signals. The technical signals for example represent the data received or outputted by the computer. The computer is preferably operatively coupled to a display device which allows information outputted by the computer to be displayed, for example to a user. One example of a display device is an augmented reality device (also referred to as augmented reality glasses) which can be used as "goggles" for navigating. A specific example of such augmented reality glasses is Google Glass (a trademark of Google, Inc.). An augmented reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific embodiment of such a computer monitor is a digital lightbox. The monitor may also be the monitor of a portable, for example handheld, device such as a smart phone or personal digital assistant or digital media player.

The expression "acquiring data" for example encompasses (within the framework of a computer implemented method) the scenario in which the data are determined by the computer implemented method or program. Determining data for example encompasses measuring physical quantities and transforming the measured values into data, for example digital data, and/or computing the data by means of a computer and for example within the framework of the method in accordance with the invention. The meaning of "acquiring data" also for example encompasses the scenario in which the data are received or retrieved by the computer implemented method or program, for example from another program, a previous method step or a data storage medium, for example for further processing by the computer implemented method or program. Generation of the data to be acquired may but need not be part of the method in accordance with the invention. The expression "acquiring data" can therefore also for example mean waiting to receive data and/or receiving the data. The received data can for example be inputted via an interface. The expression "acquiring data" can also mean that the computer implemented method or program performs steps in order to (actively) receive or retrieve the data from a data source, for instance a data storage medium (such as for example a ROM, RAM, database, hard drive, etc.), or via the interface (for instance, from another computer or a network). The data acquired by the disclosed method or device, respectively, may be acquired from a database located in a data storage device which is operably to a computer for data transfer between the database and the computer, for example from the database to the computer. The computer acquires the data for use as an input for steps of determining data. The determined data can be output again to the same or another database to be stored for later use. The database or database used for implementing the disclosed method can be located on network data storage device or a network server (for example, a cloud data storage device or a cloud server) or a local data storage device (such as a mass storage device operably connected to at least one computer executing the disclosed method). The data can be made "ready for use" by performing an additional step before the acquiring step. In accordance with this additional step, the data are generated in order to be acquired. The data are for example detected or captured (for example by an analytical device). Alternatively or additionally, the data are inputted in accordance with the additional step, for instance via interfaces. The data generated can for example be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, for example determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

The invention also relates to a program which, when running on a computer, causes the computer to perform one or more or all of the method steps described herein and/or to a program storage medium on which the program is stored (in particular in a non-transitory form) and/or to a computer comprising said program storage medium and/or to a (physical, for example electrical, for example technically generated) signal wave, for example a digital signal wave, carrying information which represents the program, for example the aforementioned program, which for example comprises code means which are adapted to perform any or all of the method steps described herein.

The invention also relates to a navigation system for computer-assisted surgery, comprising:
the computer of the preceding claim, for processing the absolute point data and the relative point data;
a detection device for detecting the position of the main and auxiliary points in order to generate the absolute point data and to supply the absolute point data to the computer;
a data interface for receiving the relative point data and for supplying the relative point data to the computer; and
a user interface for receiving data from the computer in order to provide information to the user, wherein the received data are generated by the computer on the basis of the results of the processing performed by the computer.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, for example a data processing device comprising a digital processor (central processing unit or CPU) which executes the computer program elements, and optionally a volatile memory (for example a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can for example include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which for example comprises technical, for example tangible components, for example mechanical and/or electronic components. Any device mentioned as such in this document is a technical and for example tangible device.

A landmark is a defined element of an anatomical body part which is always identical or recurs with a high degree of similarity in the same anatomical body part of multiple patients. Typical landmarks are for example the epicondyles of a femoral bone or the tips of the transverse processes and/or dorsal process of a vertebra. The points (main points or auxiliary points) can represent such landmarks. A landmark which lies on (for example on the surface of) a characteristic anatomical structure of the body part can also represent said structure. The landmark can represent the anatomical structure as a whole or only a point or part of it. A landmark can also for example lie on the anatomical structure, which is for example a prominent structure. An example of such an anatomical structure is the posterior aspect of the iliac crest. Another example of a landmark is one defined by the rim of the acetabulum, for instance by the center of said rim. In another example, a landmark represents the bottom or deepest point of an acetabulum, which is derived from a multitude of detection points. Thus, one landmark can for example represent a multitude of detection points. As mentioned above, a landmark can represent an anatomical characteristic which is defined on the basis of a characteristic structure of the body part. Additionally, a landmark can also represent an anatomical characteristic defined by a relative movement of two body parts, such as the rotational center of the femur when moved relative to the acetabulum.

The information on the imaging geometry preferably comprises information which allows the analysis image (x-ray image) to be calculated, given a known relative position between the imaging geometry analysis apparatus and the analysis object (anatomical body part) to be analyzed by x-ray radiation, if the analysis object which is to be analyzed is known, wherein "known" means that the spatial geometry (size and shape) of the analysis object is known. This means for example that three-dimensional, "spatially resolved" information concerning the interaction between the analysis object (anatomical body part) and the analysis radiation (x-ray radiation) is known, wherein "interaction" means for example that the analysis radiation is blocked or partially or completely allowed to pass by the analysis object. The location and in particular orientation of the imaging geometry is for example defined by the position of the x-ray device, for example by the position of the x-ray source and the x-ray detector and/or for example by the position of the multiplicity (manifold) of x-ray beams which pass through the analysis object and are detected by the x-ray detector. The imaging geometry for example describes the position (i.e. the location and in particular the orientation) and the shape (for example, a conical shape exhibiting a specific angle of inclination) of said multiplicity (manifold). The position can for example be represented by the position of an x-ray beam which passes through the center of said multiplicity or by the position of a geometric object (such as a truncated cone) which represents the multiplicity (manifold) of x-ray beams. Information concerning the above-mentioned interaction is preferably known in three dimensions, for example from a three-dimensional CT, and describes the interaction in a spatially resolved way for points and/or regions of the analysis object, for example for all of the points and/or regions of the analysis object. Knowledge of the imaging geometry for example allows the location of a source of the radiation (for example, an x-ray source) to be calculated relative to an image plane (for example, the plane of an x-ray detector). With respect to the connection between three-dimensional analysis objects and two-dimensional analysis images as defined by the imaging geometry, reference is made for example to the following publications:

1. "An Efficient and Accurate Camera Calibration Technique for 3D Machine Vision", Roger Y. Tsai, Proceedings of the IEEE Conference on Computer Vision and Pattern Recognition. Miami Beach, Fla., 1986, pages 364-374
2. "A Versatile Camera Calibration Technique for High-Accuracy 3D Machine Vision Metrology Using Off-the-Shelf TV Cameras and Lenses", Roger Y. Tsai, IEEE Journal of Robotics and Automation, Volume RA-3, No. 4, August 1987, pages 323-344.
3. "Fluoroscopic X-ray Image Processing and Registration for Computer-Aided Orthopedic Surgery", Ziv Yaniv
4. EP 08 156 293.6
5. U.S. 61/054,187

Preferably, atlas data is acquired which describes (for example defines, more particularly represents and/or is) a general three-dimensional shape of the anatomical body part. The atlas data therefore represents an atlas of the anatomical body part. An atlas typically consists of a plurality of generic models of objects, wherein the generic models of the objects together form a complex structure. For example, the atlas constitutes a statistical model of a patient's body (for example, a part of the body) which has been generated from anatomic information gathered from a plurality of human bodies, for example from medical image data containing images of such human bodies. In principle, the atlas data therefore represents the result of a statistical analysis of such medical image data for a plurality of human bodies. This result can be output as an image—the atlas data therefore contains or is comparable to medical image data. Such a comparison can be carried out for example by applying an image fusion algorithm which conducts an image fusion between the atlas data and the medical image data. The result of the comparison can be a measure of similarity between the atlas data and the medical image data. The atlas data comprises positional information which can be matched (for example by applying an elastic or rigid image fusion algorithm) for example to positional information contained in medical image data so as to for example compare the atlas data to the medical image data in order to determine the position of anatomical structures in the medical image data which correspond to anatomical structures defined by the atlas data.

The human bodies, the anatomy of which serves as an input for generating the atlas data, advantageously share a common feature such as at least one of gender, age, ethnicity, body measurements (e.g. size and/or mass) and pathologic state. The anatomic information describes for example the anatomy of the human bodies and is extracted for example from medical image information about the human bodies. The atlas of a femur, for example, can comprise the head, the neck, the body, the greater trochanter, the lesser trochanter and the lower extremity as objects which together make up the complete structure. The atlas of a brain, for example, can comprise the telencephalon, the cerebellum, the diencephalon, the pons, the mesencephalon and the medulla as the objects which together make up the complex structure. One application of such an atlas is in the segmentation of medical images, in which the atlas is matched to medical image data, and the image data are compared with the matched atlas in order to assign a point (a pixel or voxel)

of the image data to an object of the matched atlas, thereby segmenting the image data into objects.

In particular, the invention does not involve or in particular comprise or encompass an invasive step which would represent a substantial physical interference with the body requiring professional medical expertise to be carried out and entailing a substantial health risk even when carried out with the required professional care and expertise. For example, the invention does not comprise a step of positioning a medical implant in order to fasten it to an anatomical structure or a step of fastening the medical implant to the anatomical structure or a step of preparing the anatomical structure for having the medical implant fastened to it. More particularly, the invention does not involve or in particular comprise or encompass any surgical or therapeutic activity. The invention is instead directed as applicable to positioning a tool relative to the medical implant, which may be outside the patient's body. For this reason alone, no surgical or therapeutic activity and in particular no surgical or therapeutic step is necessitated or implied by carrying out the invention.

The present invention can be implemented, for example in navigation software for hip surgery. The software may therefore import an X-ray dataset and, on that basis, calculate the above described sagittal rotation between the X-ray image plane and an AAC-plane, which will eventually allow a navigation on a functional plane defined by the preoperative X-ray dataset.

BRIEF DESCRIPTION OF DRAWINGS

In the following, the invention is described with reference to the enclosed figures which represent preferred embodiments of the invention. The scope of the invention is not however limited to the specific features disclosed in the figures, which show.

DETAILED DESCRIPTION

Figure 1:
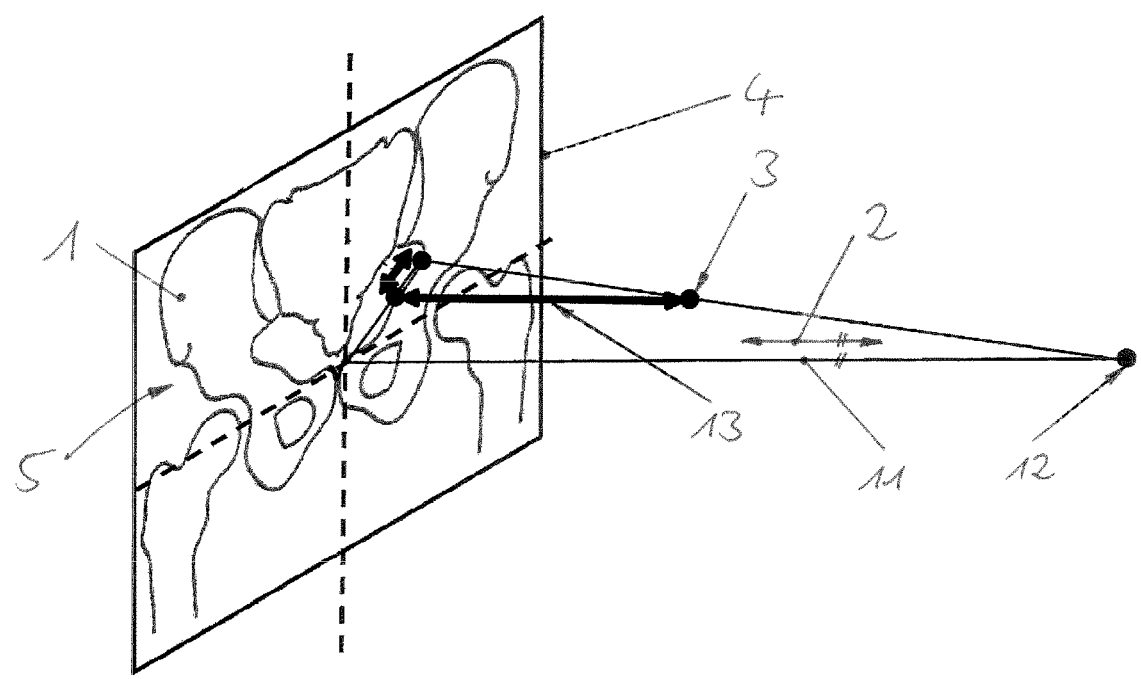
FIG. 1 a geometric setup of X-ray-imaging.
Figure 2:
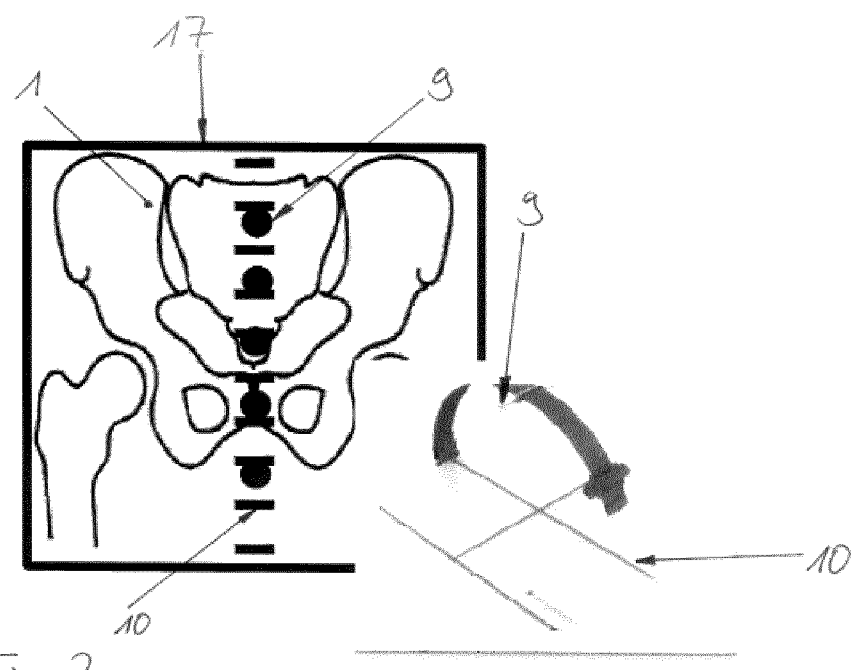
FIG. 2 an anterior-posterior X-ray-image with calibration features.

The geometric setup of a conventional X-ray-imaging method can be seen in FIG. 1. A punctual radiation source 12 emits radiation in a spherical manner, and towards a pelvis (not shown). As the emitted radiation is adsorbed by matter to a varying degree, an image 5 of the pelvis 1 forms behind the pelvis 1 in an image plane (not shown). This image is however distorted due to the spherical propagation of the emitted radiation. An exemplary landmark 3 will therefore be depicted at a position in the image which is different from a position that would have been obtained if the entire pelvis 1 is projected into the image plane in an anterior-posterior direction 2.

According to one embodiment the present invention, this positional shift or distortion is compensated for by determining the geometric setup including the distance between the X-ray-source 12 and the calibration plane 4, and the distances 13 of each of the pelvic landmarks 3 to the calibration plane 4 in the anterior-posterior direction 2.

Figure 3:
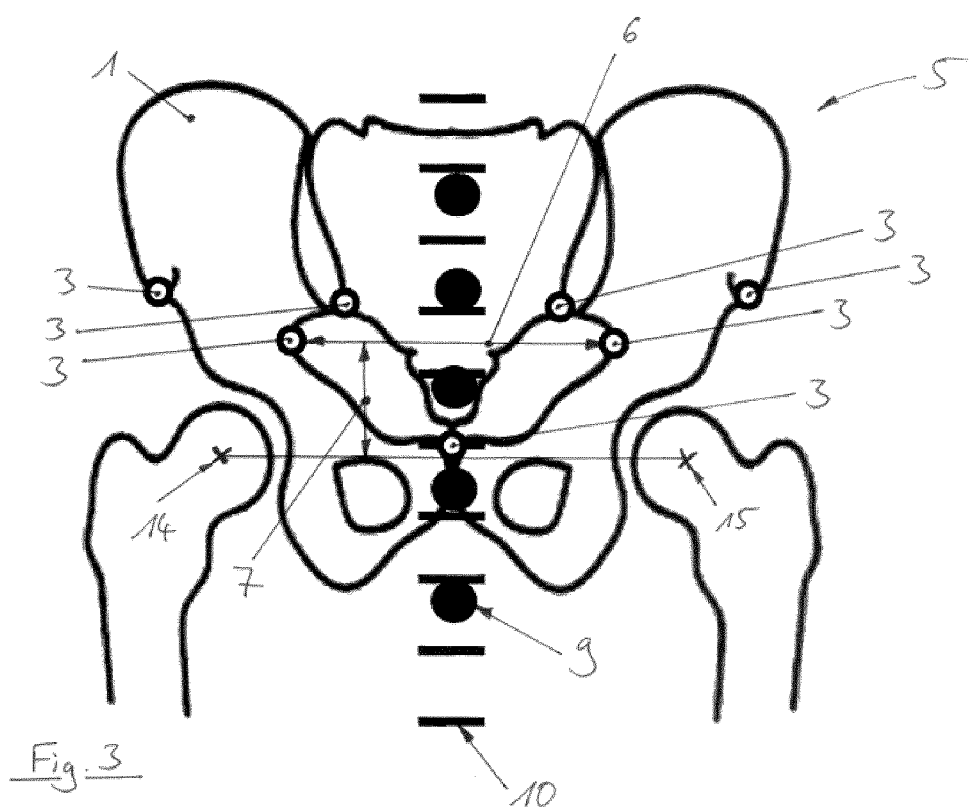
FIG. 3 shows the image of FIG. 2 with pelvic landmarks indicated.

After an X-ray-image of the patient's pelvis together with a plurality of calibration features 9, 10 has been taken in an anterior-posterior direction 2 (shown in FIG. 1), a plurality of pelvic landmarks 3, 14, 15 can then be identified either manually or automatically within the X-ray-image as shown in FIG. 3.

Figure 6:
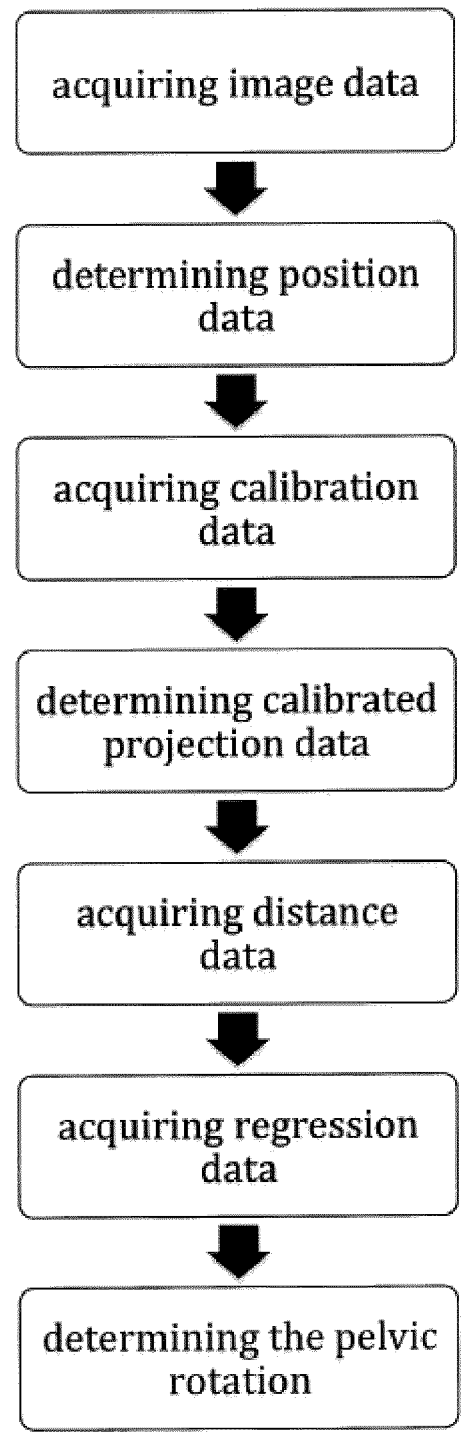
FIG. 6 the basic steps of the inventive computer implemented method.

After the X-ray-image has been "calibrated" by performing steps 2, 3, 4 and 5 of the inventive method outlined in FIG. 6, distance measurements between the pelvic landmarks 3, 14, 15 in a media-lateral direction and in a cranial-caudal direction are possible. The determined distances 6, 7 can then be compared with statistical values obtained from a plurality of reference patients.

Since a database stored on a storage medium provides a direct correlation between the distance measurements and a determined value for the sagittal rotation 8 of the pelvis 1, the sagittal rotation 8 of the current patient's pelvis can be derived from that database.

Figure 4:
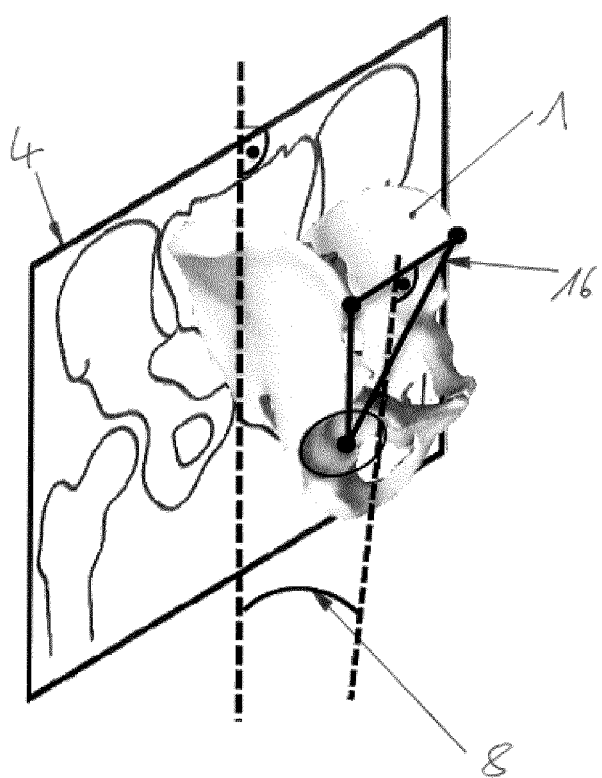
FIG. 4 a sagittal rotation angle between an X-ray plane and an AAC plane.
Figure 5:
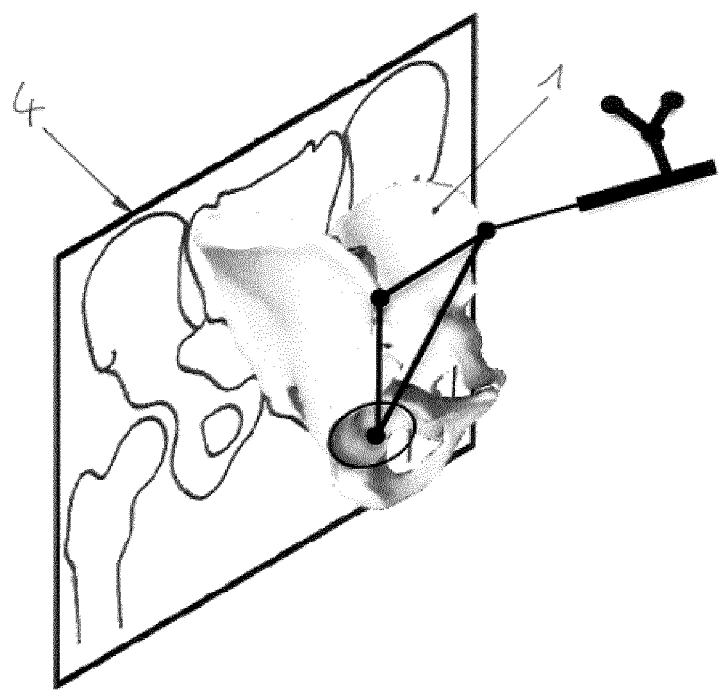
FIG. 5 a registration of an AAC-plane.

According to a preferred embodiment of the present invention, the sagittal rotation 8 defines the angle between the coronal plane 4 and an AAC-plane 16 (shown in FIG. 4). The AAC-plane 16 can serve as a reference plane for procedures following the inventive method, after the actual pelvis 1 has been registered in real space, for example by determining the spatial position of the left and the right anterior-superior iliac spine and one of the centers of rotation of the left or right acetabulum, as shown in FIG. 5.

The invention claimed is:

1. A computer implemented method for determining a sagittal rotation of a patient's pelvis, the method comprising:
   acquiring image data describing a two-dimensional X-ray-image of the patient's pelvis made in an anterior-posterior direction;
   determining, based on the image data, position data describing the position of a plurality of pelvic landmarks reproduced in or derivable from the two-dimensional X-ray-image;
   acquiring calibration data describing the position of a calibration plane with respect to the patient's pelvis, the calibration plane being perpendicular to the anterior-posterior direction;
   determining, based on the position data and the calibration data, calibrated projection data describing a two-dimensional projection representing the plurality of pelvic landmarks of the patient's pelvis being projected into the calibration plane in the anterior-posterior direction;
   acquiring distance data describing at least one of a medial-lateral distance and a cranial-caudal distance between at least one first pelvic landmark and at least one second pelvic landmark in the calibrated two-dimensional projection;
   acquiring, from a database, regression data describing a linear correspondence between at least one of said medial-lateral distances and cranial-caudal distances, and a pelvic sagittal rotation; and
   determining, based on the distance data and the regression data, the sagittal rotation of the patient's pelvis.

2. The method of claim 1, wherein the determining calibrated projection data involves the use of at least one calibration feature of a predetermined size and/or geometry, which is reproduced in the X-ray-image.

3. The method of claim 2, wherein at least one calibration feature is disposed anterior to the patient's pelvis and at least one calibration feature is disposed posterior to the patient's pelvis.

4. The method of claim 1, wherein the determining calibrated projection data comprises:
acquiring source-distance data describing the distance between the X-ray-source and the calibration plane; and
acquiring anterior-posterior-distance data describing the distance of each of the plurality of pelvic landmarks to the calibration plane in the anterior-posterior direction.

5. The method of claim 4, wherein:
predefined values are set for the anterior-posterior-distances of the plurality of pelvic landmarks, or
wherein the acquiring anterior-posterior-distance data comprises:
matching a three-dimensional pelvis model acquired from an anatomical atlas to the two-dimensional X-ray-image, the model specifying the position of the plurality of pelvic landmarks; and
identifying, based on the three-dimensional pelvis model, statistical values for the anterior-posterior-distances of the plurality of pelvic landmarks to the calibration plane in the anterior-posterior direction.

6. The method of claim 1, wherein the determining calibrated projection data comprises:
acquiring reference distance data describing the distance in the anterior-posterior direction of each of the plurality of pelvic landmarks to at least one of:
an anterior reference plane defined by the at least one calibration feature disposed anterior to the patient's pelvis; and
a posterior reference plane defined by the at least one calibration feature disposed posterior to the patient's pelvis;
acquiring plane distance data describing the distance in the anterior-posterior direction of the calibration plane to at least one of the anterior reference plane and the posterior reference plane; and
determining, based on the reference distance data and the plane distance data, anterior-posterior-distance data describing the distance of each of the plurality of pelvic landmarks to the calibration plane in the anterior-posterior direction.

7. The method of claim 1, wherein the determining position data comprises:
matching a three-dimensional pelvis model acquired from an anatomical atlas to the two-dimensional X-ray-image, the three-dimensional pelvis model specifying the position of the plurality of pelvic landmarks; and
identifying, based on the three-dimensional pelvis model, the position of the plurality of pelvic landmarks within the two-dimensional X-ray-image.

8. The method of claim 1, wherein the at least one first pelvic landmark and the at least one second pelvic landmark are selected from the group consisting of:
left anterior superior iliac spine, right anterior superior iliac spine;
left iliosacral joint, right left iliosacral;
left lateral foramen point, right lateral foramen point;
cranial edge of pubic symphysis; and
center of rotation of left acetabulum, center of rotation of right acetabulum.

9. The method of claim 1, wherein the at least one of the medial-lateral distance and the cranial-caudal distance between the at least one first pelvic landmark and the at least one second pelvic landmark are selected from the group consisting of:
medial-lateral distance between left anterior superior iliac spine and right anterior superior iliac spine;
medial-lateral distance between iliosacral joint and line connecting anterior superior iliac spines;
cranial-caudal distance between center of rotation of left or right acetabulum and line connecting anterior superior iliac spines;
cranial-caudal distance between center of rotation of left or right acetabulum and intersection point of midsagittal plane and line connecting left lateral foramen point and right lateral foramen point;
medial-lateral distance between center of rotation of left or right acetabulum and midsagittal plane of patient; and
cranial-caudal distance between center of rotation of left or right acetabulum and cranial edge of pubic symphysis.

10. The method of claim 1, wherein the two-dimensional X-ray-image shows the patient's pelvis of the patient taking a standing posture.

11. The method of claim 1, wherein the regression data is based on measurements acquired from a plurality of reference patients, wherein for each one of the reference patients, a correspondence between a pelvic sagittal rotation and at least one of a medial-lateral distance and a cranial-caudal distance between the at least one first pelvic landmark and the at least one second pelvic landmark within the calibration plane is described.

12. The method of claim 1, wherein the sagittal rotation of the patient's pelvis defines the angle between the coronal plane of the patient and an AAC-plane containing the left anterior superior iliac spine, the right anterior superior iliac spine, and at least one of the center of rotation of the left acetabulum and the center of rotation of the right acetabulum.

13. The method of claim 12, wherein the determined AAC-plane is passed on, for further use as a reference basis, to a registration procedure for surgery.

14. A system for determining a sagittal rotation of a patient's pelvis, comprising:
a computer configured to:
acquire image data describing a two-dimensional X-ray-image of the patient's pelvis made in an anterior-posterior direction;
determine, based on the image data, position data describing the position of a plurality of pelvic landmarks reproduced in or derivable from the two-dimensional X-ray-image;
acquire calibration data describing the position of a calibration plane with respect to the patient's pelvis, the calibration plane being perpendicular to the anterior-posterior direction;
determine, based on the position data and the calibration data, calibrated projection data describing a two-dimensional projection representing the plurality of pelvic landmarks of the actual patient's pelvis being projected into the calibration plane in the anterior-posterior direction;
acquire distance data describing at least one of a medial-lateral distance and a cranial-caudal distance between at least one first pelvic landmark and at least one second pelvic landmark in the calibrated two-dimensional projection;
acquire, from a database, regression data describing a linear correspondence between at least one of said medial-lateral distances and cranial-caudal distances, and a pelvic sagittal rotation; and
determine, based on the distance data and the regression data, the sagittal rotation of the patient's pelvis.

15. The system of claim 14, wherein the determining calibrated projection data involves the use of at least one calibration feature of a predetermined size and/or geometry, which is reproduced in the X-ray-image.

16. The system of claim 15, wherein at least one calibration feature is disposed anterior to the patient's pelvis and at least one calibration feature is disposed posterior to the patient's pelvis.

17. The system of claim 14, wherein the determining calibrated projection data comprises:
   acquiring source-distance data describing the distance between the X-ray-source and the calibration plane; and
   acquiring anterior-posterior-distance data describing the distance of each of the plurality of pelvic landmarks to the calibration plane in the anterior-posterior direction.

18. The system of claim 14, wherein the determining calibrated projection data comprises:
   acquiring reference distance data describing the distance in the anterior-posterior direction of each of the plurality of pelvic landmarks to at least one of:
      an anterior reference plane defined by the at least one calibration feature disposed anterior to the patient's pelvis; and
      a posterior reference plane defined by the at least one calibration feature disposed posterior to the patient's pelvis;
   acquiring plane distance data describing the distance in the anterior-posterior direction of the calibration plane to at least one of the anterior reference plane and the posterior reference plane;
   determining, based on the reference distance data and the plane distance data, anterior-posterior-distance data describing the distance of each of the plurality of pelvic landmarks to the calibration plane in the anterior-posterior direction.

19. The system of claim 14, wherein the determining position data comprises:
   matching a three-dimensional pelvis model acquired from an anatomical atlas to the two-dimensional X-ray-image, the three-dimensional pelvis model specifying the position of the plurality of pelvic landmarks; and
   identifying, based on the three-dimensional pelvis model, the position of the plurality of pelvic landmarks within the two-dimensional X-ray-image.

20. A non-transitory computer readable storage medium storing a computer program for determining a sagittal rotation of a patient's pelvis which, when running on a computer or loaded onto the computer, causes the computer to:
   acquire image data describing a two-dimensional X-ray-image of the patient's pelvis made in an anterior-posterior direction;
   determine, based on the image data, position data describing the position of a plurality of pelvic landmarks reproduced in or derivable from the two-dimensional X-ray-image;
   acquire calibration data describing the position of a calibration plane with respect to the patient's pelvis, the calibration plane being perpendicular to the anterior-posterior direction;
   determine, based on the position data and the calibration data, calibrated projection data describing a two-dimensional projection representing the plurality of pelvic landmarks of the patient's pelvis being projected into the calibration plane in the anterior-posterior direction;
   acquire distance data describing at least one of a medial-lateral distance and a cranial-caudal distance between at least one first pelvic landmark and at least one second pelvic landmark in the calibrated two-dimensional projection;
   acquire, from a database, regression data describing a linear correspondence between at least one of said medial-lateral distances and cranial-caudal distances, and a pelvic sagittal rotation; and
   determine, based on the distance data and the regression data, the sagittal rotation of the patient's pelvis.

* * * * *

UNITED STATES PATENT AND TRADEMARK OFFICE
CERTIFICATE OF CORRECTION

| | | |
|---|---|---|
| PATENT NO. | : 10,869,724 B2 | Page 1 of 1 |
| APPLICATION NO. | : 16/306991 | |
| DATED | : December 22, 2020 | |
| INVENTOR(S) | : Beck et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 108 days.

Signed and Sealed this
Seventh Day of February, 2023

Katherine Kelly Vidal
*Director of the United States Patent and Trademark Office*